United States Patent [19]

Srivastava et al.

[11] Patent Number: 4,755,375
[45] Date of Patent: Jul. 5, 1988

[54] METHOD AND KIT FOR THE SELECTIVE LABELING OF RED BLOOD CELLS IN WHOLE BLOOD WITH TC-99M

[75] Inventors: Suresh C. Srivastava, Setauket, N.Y.; John W. Babich, Redhill, England; Rita Straub, Brookhaven, N.Y.; Powell Richards, New Bern, N.C.

[73] Assignee: Associated Universities, Inc., Washington, D.C.

[21] Appl. No.: 853,120

[22] Filed: Apr. 17, 1986

Related U.S. Application Data

[63] Continuation-in-part of Ser. No. 574,486, Jan. 27, 1984, abandoned.

[51] Int. Cl.$^4$ .................... A61K 49/02; A61K 49/00; A61B 6/00
[52] U.S. Cl. ........................... 424/1.1; 424/9; 128/654; 128/659; 604/4
[58] Field of Search .............. 424/1.1, 9; 534/14; 422/61; 604/4; 128/1.1, 654, 655, 659

[56] References Cited

U.S. PATENT DOCUMENTS

| | | | |
|---|---|---|---|
| 3,725,295 | 4/1973 | Echelman et al. | 424/1.1 |
| 3,988,429 | 10/1976 | Richards et al. | 424/1.1 |
| 3,991,173 | 11/1976 | Sinn et al. | 424/1.1 |
| 4,097,238 | 6/1978 | Ashley | 424/1.1 |
| 4,300,569 | 11/1981 | Bonneau | 424/1.1 |
| 4,313,928 | 2/1982 | Kato et al. | 424/1.1 |
| 4,342,740 | 8/1982 | Narra et al. | 424/1.1 |
| 4,372,294 | 2/1983 | Strauss et al. | 424/1.1 |
| 4,443,426 | 4/1984 | Thakur | 424/1.1 |
| 4,692,324 | 9/1987 | Davis et al. | 424/1.1 |

OTHER PUBLICATIONS

Srivasta et al., Abstract, Society of Nuclear Medicine, 30th Annual Meeting, St. Louis, Jun., 1983.

Larson et al., Eur. J. Nuclear Medicine, 3, 227–231 (1978).

Porter et al., J. Nuclear Medicine, 24(5), 383–387 (1983).

*Primary Examiner*—John F. Terapane
*Assistant Examiner*—J. E. Thomas
*Attorney, Agent, or Firm*—Margaret C. Bogosian

[57] ABSTRACT

Disclosed herein are a method and kit for the preparation of $^{99m}$Tc labeled red blood cells using whole blood in a closed sterile system containing stannous tin in a form such that it will enter the red blood cells and be available therein for the reduction of technetium.

16 Claims, No Drawings

METHOD AND KIT FOR THE SELECTIVE LABELING OF RED BLOOD CELLS IN WHOLE BLOOD WITH TC-99M

The U.S. Government has rights in this invention pursuant to Contract Number DE-AC02-76CH00016, between the U.S. Department of Energy and Associated Universities Inc.

RELATED APPLICATIONS

This application is a continuation-in-part application of co-pending patent application Ser. No. 574,486 filed Jan. 27, 1984, now abandoned.

BACKGROUND OF THE INVENTION

Technetium-99m ($^{99m}$Tc) labeled red blood cells have been widely employed in humans in applications such as nuclear cardiology, blood pool imaging, red cell mass determination, spleen imaging, accessory spleen localization, detection of gastrointestinal bleeding and hemangiomas.

A procedure for labeling red blood cells is described in U.S. Pat. No. 3,988,429, entitled "Kit for the Rapid Preparation of Tc$^{99m}$ Red Blood Cells", issued Oct. 26, 1976 to Powell Richards, et al. This procedure comprises the steps of supplying a sample of blood to a previously prepared, partially evacuated container containing a dry mixture of an anticoagulant and a reagent for supplying stannous ion, dissolving the dry mixture in the blood, and adding a sterile saline solution. The resulting solution containing suspended red blood cells is centrifuged to form a layer of packed red blood cells, some of which are collected. The collected cells are then mixed with a previously prepared saline solution of $^{99m}$Tc sodium pertechnetate to effect the labeling.

The procedure disclosed in the above identified patent has been widely used for a number of years. However, it is somewhat cumbersome and requires considerable handling of the reagents. In addition, it has the significant disadvantage of requiring separation of the red blood cells from the plasma.

The instant invention overcomes the disadvantages of the prior art by providing a method of labeling red blood cells with $^{99m}$Tc which (1) eliminates the need for separating plasma; (2) requires no centrifugation and greatly reduces handling of the cells; (3) may be conducted in one vessel without transfers, thus facilitating the maintenance of aseptic conditions; (4) tolerates greater quantities of $^{99}$Tc contamination in $^{99m}$Tc eluates from the generator; and (5) is more convenient to carry out in practice.

SUMMARY OF THE INVENTION

The present invention comprises a method of labeling red blood cells with technetium-99m and a kit that is designed to permit the practice of this method in the clinical setting. This method provides a simplified and reproducible procedure for labeling red blood cells with technetium-99m using small whole blood samples containing red blood cells and plasma.

In broad outline, the labeling method of the present invention comprises the steps of:

A. drawing a small sample of the patient's blood, between 0.5 ml and 6 ml, preferably about 1.0 ml, into a syringe which may contain an anti-coagulant agent such as heparin;

B. supplying this blood sample to a container having therein under sterilized conditions a lyophilized stannous ion complex with a tin content of from 5 to 100 μg. The stannous ion is in the form of a tin complex with a suitable complexing agent. This container additionally contains a tin complex stabilizer and may contain an anti-coagulant in case the blood sample was not drawn into an anti-coagulant coated syringe;

C. subjecting the resulting suspenion to the action of an oxidizing agent to convert substantially all of the stannous tin remaining in the plasma to the oxidized stannic form;

D. incubating the suspension with a chelating agent to help with the chelation and further oxidation of the remaining traces of stannous tin; and E. incubating the resulting suspension with a source of $^{99m}$Tc pertechnetate ion to permit the ion to pass through the cell membranes of the red blood cells and into the cells for a sufficient period of time to permit the stannous ions within the red blood cells to reduce the technetium to a lower valence state in which it will not pass out of the cell, thereby labeling the red blood cells with $^{99m}$Tc.

The radioactive technetium used in the labeling process and clinical kit disclosed herein may be obtained by means of an elution process using a $^{99m}$Tc generator, the construction and use of which is well known and understood.

In Step B above, a substantial amount of the stannous tin in the form of a complex with a selected ligand passes through the cell membranes into the red blood cells where it is available to reduce the technetium.

A certain amount of the tin remains in the plasma in the stannous form. It should be eliminated so that it does not reduce the technetium before it enters the red blood cells, thereby reducing the yield of labeled cells. This is accomplished in Step C by oxidation using any convenient reagent which will accomplish the oxidation without entering the red blood cells so that the stannous ion within the cell remains available to reduce the technetium. It is convenient to follow the oxidation step with a chelating agent which will scavenge the plasma of the remaining tin ion by forming a tin chelate and/or help in further oxidation of the remaining stannous tin.

Labeling efficiencies of over 95% are routinely observed using this method, and there is no necessity for separating the red blood cells from the plasma during labeling so that the intact blood sample is available for reinjection into the patient.

A further embodiment of the present invention is a red blood cell labeling kit that permits the above described labeling method to be carried out in the clinical setting. This kit will comprise a container in which the labeling will be carried out. The container will contain, under sterilized conditions, a lyophilized stannous ion complex with a tin content of from 5 to 100 μg together with an inert stabilizing agent such as dextrose. This container may also contain an anti-coagulant.

It is most convenient that said container be penetrable with a needle and be partially evacuated so that the blood sample can be directly drawn into it. However, this construction is not essential.

DESCRIPTION OF THE PREFERRED EMBODIMENTS

A kit prepared for use in accordance with this invention comprises a reagent tube or vial containing under sterilized conditions a lyophilized stannous ion complex with a tin content of from 5 to 100 μg together with an inert stabilizing agent, such as dextrose.

The presently preferred reagent tube is a sterile sealed container equipped with a stopper penetrable with a hypodermic needle and partially evacuated to draw the amount of blood desired. Such tubes are available commercially. One such tube is the Vacutainer, a registered trademark of Becton-Dickinson. Other containers such as 10 ml sterile multi-injection vial may be used instead.

As prepared and ready for use, said sealed container may also contain an anti-coagulant. Alternatively, and preferably, the syringe used for drawing the patient's blood is coated with an anti-coagulant, preferably a dilute heparin solution, so that approximately 100 units of heparin, or an equivalent amount of another anti-coagulant, are present in the syringe before drawing blood. Anti-coagulants equivalent to heparin for this purpose include, for example, citrate phosphate dextrose (CPD), citrate phosphate dextrose and adenine (CPDA), and acid citrate dextrose (ACD). Ethylenediaminetetraacetic acid (EDTA) or oxalate are not recommended.

Complexed tin in stannous form is required for optimum performance of the labeling method of the present invention and therefore for optimum operation of the red blood cell labeling kit of this invention. The presently preferred complexing agents are citrate or glucoheptonate, normally employed as alkali metal salts, preferably as the sodium salts, or as alkaline earth metal salts, preferably as the calcium salts. However, other complexing agents such as alkali metal tartrates, pyrophosphates, organic diphosphonates such as methylene diphosphonate, EDTA, diethylenetriaminepentaacetic acid (DTPA), or dimercaptosuccinic acid (DMSA), for example, may be employed. A 15–1000 fold molar excess of the complexing agent over tin is normally employed to keep the tin tightly complexed.

The stannous ion will thus normally be present in the kit complexed with the selected reagent, preferably in the form of stannous citrate or stannous glucoheptonate.

The presently preferred inert ingredient used in the sealed container of the kit as a stabilizer is dextrose because it is readily available in highly purified form and gives good results. However, other reducing sugars such as mannose or sorbitose may also be employed. These serve to stabilize and prevent the hydrolysis of the tin. They also serve as inexpensive fillers for the kit and assist in maintaining a proper osmolality in the system so that the cells are not damaged.

The tin content of the kits can vary over a wide range, for example from 5 to 100 μg. The molar ratio of complexing agent to stannous tin may be as low as 15:1 or as high as 1000:1. The dextrose to tin molar ratio may range between 35:1 and 750:1. Appreciable variations from these ranges may be tolerated without unacceptably adverse results. The preferred ratio for sodium citrate or glucoheptonate is from 15:1 to 300:1, and for dextrose or other reducing sugar to tin, it is from 70:1 to 725:1.

EXAMPLE 1

Procedure For The Preparation Of The Red Blood Cell Labeling Kit (containing 50 μg tin) Of The Present Invention 1. Add 630 mg (about 37 mm of 0.5 mm diameter) tin wire to a 25 ml volumetric flask and transfer to $N_2$ glove box.
2. Add 5.0 ml conc. HCl to 25 ml volumetric flask containing tin wire, and cover mouth of flask with small beaker. Heat gently, but do not boil.
3. When the tin is dissolved, dilute to volume with previously boiled sterile water. This is solution A containing about 25 mg/ml Sn (II) in about 2.4 N HCl. (Up to 10% of tin may be present in the stannic form.)
4. Dissolve 36.70 g of trisodium citrate dihydrate in about 80 ml of water in a 200 ml beaker.
5. Add 20 ml of solution A to the citrate solution dropwise, mixing well and holding the pH between 6 and 7.5 by adding 1N NaOH. Adjust the final pH to 7 to 7.5. This procedure is best monitored with a pH meter.
6. Quantitatively transfer solution from Step 5 to a 200 ml volumetric flask and dilute to volume with sterile water. This is solution B containing about 2.5 mg/ml Sn (II), and 183.5 mg/ml trisodium citrate, dihydrate.
7. Aseptically transfer 13 ml aliquots of solution B via sterile needle and syringe into sterile 30 ml multi-injection bottles. Quick freeze the bottles containing solution B and store in a deep freezer until ready for use.
8. For preparing a batch of kits, allow one 30 ml bottle containing 13 ml frozen stannous citrate to come to room temperature just before use. Transfer 10.0 ml of this solution into a 250 ml volumetric flask containing 2.75 g anhydrous dextrose dissolved in sterile water. Dilute to volume. This is solution C containing 100 μg/ml Sn (II), 11.0 mg/ml dextrose, and 7.34 mg/ml trisodium citrate, dihydrate.
9. Remove solution C from glove box after filtering through sterile 0.22 μm Millipore filter into sterile dispenser.
10. Dispense 0.5 ml of solution C into sterile Vacutainer® tubes and immediately freeze using dry ice.
11. Freeze dry and close tubes remotely under partial vacuum ($N_2$).
12. It is preferred, although not essential, to complete sterilization of the kit tubes with 2.5 megarads $^{60}Co$.

Each kit thus prepared will contain about:
50.0 μg tin (>80% as stannous tin)
3.67 mg trisodium citrate dihydrate
5.5 mg anhydrous dextrose
1.4 mg sodium chloride (maximum)

Those skilled in the art can readily devise procedures employing equivalent reagents of the types disclosed herein.

EXAMPLE 2

Procedure For The Use Of Kits Prepared In Accordance With The Procedures Described In Example 1 To Label Red Blood Cells In Whole Blood With $^{99m}Tc$ 1. Provide selected amount of whole blood (0.5 to 6ml, preferably 1 ml) to the reagents in the sealed container kit (normally by drawing the blood from the patient into a syringe, coated with an anti-congulant, such as heparin), and incubate for about 5 minutes.
2. Add 0.6 ml of 0.1% sodium hypochlorite solution in saline and mix gently by inverting the tube 4–5 times.

3. Add 1.0 ml of an ACD solution or of a 4.4% EDTA solution (disodium salt or calcium disodium salt) and mix gently by inverting the tube 4–5 times.

4. Add desired quantity of $^{99m}$Tc pertechnetate in saline in a volume of 0.5 to 3 ml and incubate for about 15–20 minutes with occasional gentle mixing.

5. The suspension is assayed and diluted appropriately if necessary, before re-injection into the patient. Cell separation and assay as described below normally give a labeling yield of greater than 95%.

The reaction periods mentioned above are convenient, but not critical. The criterion for the reaction time in each step is that it be sufficiently long to effect the desired result.

The $^{99m}$Tc labeled red blood cells prepared in this manner are useful for imaging of the blood pool, for localization of gastrointestinal bleeding sites, for red cell mass determinations and for other medical applications. For spleen imaging, the labeled cells should be damaged. This is accomplished by conducting Step 4 above at an elevated temperature, typically about 49° C. It has been observed that this will damage most of the cells, which is sufficient for spleen imaging. The red blood cell labeling method of the present invention can therefore be used to produce a labeled blood sample for re-injection where the cells are undamaged, for use in a variety of imaging applications, or a labeled blood sample for re-injection where the cells are damaged, for use in spleen imaging.

During Step 1 of the labeling procedure above, the stannous complex passes through the cell membrane into the cell where it will be available to label the cell by reducing the $^{99m}$TcO$_4$ when the latter passes through the cell membrane in Step 4. As indicated above, a certain amount (traces) of the stannous tin may remain in the plasma and reduce the $^{99m}$TcO$_4$— before it passes the cell membrane. The function of the hypochlorite and the chelating agent of Steps 2 and 3, respectively, is to oxidize, or at least partly oxidize, and chelate the stannous tin in the plasma so that the technetium is not reduced until it is inside the cell.

It will be apparent to those skilled in the art that oxidizing agents other than NaOCl or other than alkali metal hypochlorites can be employed and that tin chelating agents other than ACD, Na$_2$EDTA or CaNa$_2$EDTA will be useful. These reagents, however, are particularly preferred because they are readily available in physiologically acceptable form and have been previously utilized in many pharmaceutical preparations. A particular advantage of NaOCl as an oxidizing agent is that it will not pass through the cell membrane. In addition, it is readily consumed by stannous tin and organics in the plasma to produce stannic ions.

In the foregoing procedure, the concentration of the sodium hypochlorite is given as 0.1%. This is a convenient concentration, but clearly it can vary appreciably within certain limits, the only criterion being that for optimum performance it should be sufficient to oxidize all of the stannous tin in the plasma and not cause cell hemolysis. A convenient procedure for the preparation of the hypochlorite solution is to dilute reagent grade NaOCl (for example, J. T. Baker, Reagent NaOCl, 5.25%) with isotonic saline to give a 0.1% final concentration.

The pH of the ACD, Na$_2$EDTA, or CaNa$_2$EDTA can vary over a wide range, from 4 to 8. Commercial ACD (pH 5–7) or commercial EDTA for injection (disodium EDTA or calcium disodium EDTA) adjusted to pH 7 are suitable. A 4.4% solution of Na$_2$EDTA for use in this invention if prepared by dissolving the reagent in water generally has a pH between 4 and 5.

EXAMPLE 3

Determination Of The Labeling Yields

Draw an aliquot (0.1 to 0.5 ml) of the well-mixed labeled red blood cell suspension into a syringe and add to a tube containing 2 ml saline. Mix briefly and centrifuge for 5 minutes at 1300 G. Withdraw the supernatant solution carefully with a long disposable Pasteur pipet or spinal needle and transfer to another tube. Make volumes in both tubes equal with water. Count supernatant solution and red blood cells (RBC) and calculate the yield as follows:

$$\text{percent labeling yield} = \frac{\text{Activity in } RBC \times 100}{\text{Activity in } RBC + \text{Activiy in Supernatant Solution}}$$

The $^{99m}$Tc activity should be measured in a dose calibrator unless the sample has been allowed to cool down to 1 $\mu$Ci or less in which case a NaI gamma counter can be used.

As indicated above, the most convenient source of pertechnetate ion is the known technetium generator which provides the technetium as a solution of alkali metal pertechnetate, normally the sodium salt. The technetium ion is obtained from the generator as a mixture of $^{99m}$Tc and $^{99}$Tc generated by decay of $^{99}$Mo. In the practice of this invention, the number of technetium atoms added to the kit can be sufficiently high so that under normal usage, it is not necessary to monitor the $^{99m}$Tc eluates for their total technetium content.

We claim:

1. A method of labeling red blood cells with $^{99m}$Tc consisting essentially of:
   A. supplying a sample of whole blood, including plasma and the red blood cells to be labeled, to a container having therein under sterilized conditions a lyophilized stannous ion complex with a tin content of from 5–1000 $\mu$g together with a tin complex stabilizer and incubating the mixture for a sufficient time to permit some of the stannous ion complex to pass through the membranes of the red blood cells into the cells;
   b. subjecting the resulting suspension of red blood cells in plasma to the action of an oxidizing agent to convert substantially all of the stannous tin in the plasma to stannic tin;
   C. incubating the avove suspension with a chelating agent for both stannic and residual stannous tin in the plasma to form tin chelates; and
   D. incubating the resulting suspension with a source of $^{99m}$Tc pertechnetate ion, in a form in which the ion will pass through the cell membranes of the red blood cells into the red blood cells, for a sufficient period of time to permit the stannous ions within the red blood cells to reduce the technetium to a lower valence state in which it will not pass out of the cells through the cell membrane, thereby labeling the cells with $^{99m}$Tc.

2. A method as in claim 1 wherein the whole blood is treated with an anti-coagulant agent before it enters the container.

3. The method of claim 2 wherein the anti-coagulant agent is heparin.

4. A method as in claim 1 wherein said container also contains an anti-coagulant so that the whole blood is prevented from coagulating by the action of said anti-coagulant in the container.

5. A method as in claim 1 wherein the stannous ion is complexed with a complexing agent selected from the group consisting of alkali metal citrates, alkali metal glucoheptonates, alkaline earth metal citrates, alkaline earth metal glucoheptonates, alkali metal tartrates, alkali metal pyrophosphates, organic diphosphonates, ethylenediaminetetraacetic acid, dimercaptosuccinic acid and diethylenetriaminepentaacetic acid.

6. The method of claim 5 wherein the complexing agent is sodium citrate.

7. The method of claim 5 wherein the complexing agent is sodium glucoheptonate.

8. A method of claim 1 wherein the tin complex stabilizer is a reducing sugar.

9. The method of claim 8 wherein the reducing sugar is dextrose.

10. A method of claim 1 wherein the oxidizing agent is an alkali metal hypochlorite.

11. A method of claim 1 wherein the chelating agent is selected from the group consisting of disodium ethylenediaminetetraacetic acid, calcium disodium ethylenediaminetetraacetic acid, and acid citrate dextrose.

12. A method of claim 1 wherein the source of the $^{99m}$Tc pertechnetate ion is an alkali metal pertechnetate.

13. The method of claim 1 wherein the complexing agent is selected from the group consisting of sodium citrate and sodium glucophetonate, the tin complex stabilizer is dextrose, the oxidizing agent is an alkali metal hypochlorite, the chelating agent is selected from the group consisting of disodium ethylenediaminetetraacetic acid, calcium disodium ethylenediaminetetraacetic acid, and acid citrate dextrose, and the source of the $^{99m}$Tc pertechnetate ion is an alkali metal pertechnetate.

14. A method as in claim 13 wherein the oxidizing agent is sodium hypochlorite and the source of $^{99m}$Tc pertechnetate ion is sodium pertechnetate.

15. A method as in claim 1 wherein the incubation of Step D is conducted at an elevated temperature to damage the labeled red blood cells.

16. A method as in claim 13 wherein the incubation of Step D is conducted at an elevated temperature to damage the labeled red blood cells.

* * * * *